(12) United States Patent
Sulsky et al.

(10) Patent No.: US 6,573,287 B2
(45) Date of Patent: Jun. 3, 2003

(54) 2,1-OXAZOLINE AND 1,2-PYRAZOLINE-BASED INHIBITORS OF DIPEPTIDYL PEPTIDASE IV AND METHOD

(75) Inventors: Richard B. Sulsky, West Trenton, NJ (US); Jeffrey A. Robl, Newtown, PA (US)

(73) Assignee: Bristo-Myers Squibb Company, Princeton, NJ (US)

( * ) Notice: Subject to any disclaimer, the term of this patent is extended or adjusted under 35 U.S.C. 154(b) by 0 days.

(21) Appl. No.: 10/107,279

(22) Filed: Mar. 26, 2002

(65) Prior Publication Data
US 2002/0183367 A1 Dec. 5, 2002

Related U.S. Application Data

(60) Provisional application No. 60/283,438, filed on Apr. 12, 2001.

(51) Int. Cl.$^7$ .................... A61K 31/415; C07D 231/06
(52) U.S. Cl. .................... 514/378; 548/379.4; 548/240; 514/406
(58) Field of Search .............................. 548/240, 379.4; 514/406, 378

(56) References Cited

PUBLICATIONS

Mish, M.R. et al, J. Am. Chem. Soc., 229, 8379–8380, (1997).
Vasella, A. et al, Helvetica Chimica Acta, vol. 66, Fasc. 4, Nr. 121, 1241–1252, (1983).

Primary Examiner—Joseph K. McKane
Assistant Examiner—Golam M. M. Shameem
(74) Attorney, Agent, or Firm—Burton Rodney

(57) ABSTRACT

Dipeptidyl peptidase IV (DP 4) inhibiting compounds are provided having the formula

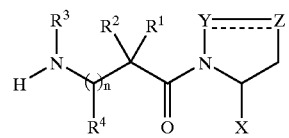

where n is 0 or 1; X is H or CN;

Y is N, NH or O;

Z is $CH_2$ when Y is O or N—H, with Y—Z forming a single bond, and Z is CH when Y is N, with Y—Z forming a double bond;

and wherein $R^1$, $R^2$, $R^3$ and $R^4$ are as described herein.

A method is also provided for treating diabetes and related diseases, especially Type II diabetes, and other diseases as set out herein, employing such DP 4 inhibitor or a combination of such DP 4 inhibitor and one or more of another antidiabetic agent such as metformin, glyburide, troglitazone, pioglitazone, rosiglitazone and/or insulin and/or one or more of a hypolipidemic agent and/or anti-obesity agent and/or other therapeutic agent.

9 Claims, No Drawings

2,1-OXAZOLINE AND 1,2-PYRAZOLINE-BASED INHIBITORS OF DIPEPTIDYL PEPTIDASE IV AND METHOD

This application claims priority to U.S. provisional application No. 60/283,438 filed Apr. 12, 2001, the entirety of which is incorporated herein by reference.

FIELD OF THE INVENTION

The present invention relates to oxazoline and pyrazoline-based inhibitors of dipeptidyl peptidase IV (DP-4), and to a method for treating diabetes, especially Type II diabetes, as well as impaired glucose homeostasis, impaired glucose tolerance, infertility, polycystic ovary syndrome, growth disorders, frailty, arthritis, allograft rejection in transplantation, autoimmune diseases, AIDS, intestinal diseases, inflammatory bowel syndrome, anorexia nervosa, osteoporosis, hyperglycemia, Syndrome X, diabetic complications, hyperinsulinemia, obesity, atherosclerosis and related diseases, as well as various immunomodulatory diseases and chronic inflammatory bowel disease (such as Crohn's disease and ulcerative colitis), employing such oxazoline and pyrazoline-based inhibitors alone or in combination with another type antidiabetic agent and/or other type therapeutic agent.

BACKGROUND OF THE INVENTION

Dipeptidyl peptidase IV (DP-4) is a membrane bound non-clasical serine aminodipeptidase which is located in a variety of tissues (intestine, liver, lung, kidney) as well as on circulating T-lymphocytes (where the enzyme is known as CD-26). It is responsible for the metabolic cleavage of certain endogenous peptides (GLP-1(7–36), glucagon) in vivo and has demonstrated proteolytic activity against a variety of other peptides (GHRH, NPY, GLP-2, VIP) in vitro.

GLP-1(7–36) is a 29 amino-acid peptide derived by post-translational processing of proglucagon in the small intestine. GLP-1(7–36) has multiple actions in vivo including the stimulation of insulin secretion, inhibition of glucagon secretion, the promotion of satiety, and the slowing of gastric emptying. Based on its physiological profile, the actions of GLP-1(7–36) are expected to be beneficial in the prevention and treatment of type II diabetes and potentially obesity. To support this claim, exogenous administration of GLP-1(7–36) (continous infusion) in diabetic patients has demonstrated efficacy in this patient population. Unfortunately GLP-1(7–36) is degraded rapidly in vivo and has been shown to have a short half-life in vivo (t1/2≈1.5 min). Based on a study of genetically bred DP-4 KO mice and on in vivo/in vitro studies with selective DP-4 inhibitors, DP-4 has been shown to be the primary degrading enzyme of GLP-1(7–36) in vivo. GLP-1(7–36) is degraded by DP-4 efficiently to GLP-1(9–36), which has been speculated to act as a physiological antagonist to GLP-1(7–36). Thus, inhibition of DP-4 in vivo should potentiate endogenous levels of GLP-1(7–36) and attenuate formation of its antagonist GLP-1(9–36) and thus serve to ameliorate the diabetic condition.

DESCRIPTION OF THE INVENTION

In accordance with the present invention, oxazoline and pyrazoline-based compounds are provided which inhibit DP-4 and have the structure I

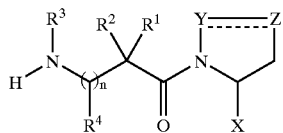

wherein n is 0 or 1;

X is H or CN (that is cyano);

Y is N, N—H or O;

Z is $CH_2$ when Y is O or N—H, Y—Z forming a single bond and

Z is CH when Y is N, Y—Z forming a double bond provided that Y—Z≠NH—$CH_2$ when X is H;

$R^1$, $R^2$, $R^3$ and $R^4$ are the same or different and are independently selected from H, alkyl, alkenyl, alkynyl, cycloalkyl, cycloalkylalkyl, bicycloalkyl, bicycloalkylalkyl, alkylthioalkyl, arylalkylthioalkyl, cycloalkenyl, aryl, aralkyl, heteroaryl, heteroarylalkyl, cycloheteroalkyl and cycloheteroalkylalkyl, all optionally substituted through available carbon atoms with 1, 2, 3, 4 or 5 groups selected from hydrogen, halo, alkyl, polyhaloalkyl, alkoxy, haloalkoxy, polyhaloalkoxy, alkoxycarbonyl, hydroxy, alkylhydroxy, alkenyl, alkynyl, cycloalkyl, cycloalkylalkyl, polycycloalkyl, heteroarylamino, arylamino, cycloheteroalkyl, cycloheteroalkylalkyl, hydroxy, hydroxyalkyl, nitro, cyano, amino, substituted amino, alkylamino, dialkylamino, thiol, alkylthio, alkylcarbonyl, acyl, alkoxycarbonyl, aminocarbonyl, alkynylaminocarbonyl, alkylaminocarbonyl, alkenylaminocarbonyl, alkylcarbonyloxy, alkylcarbonylamino, arylcarbonylamino, alkylsulfonylamino, alkylaminocarbonylamino, alkoxycarbonylamino, alkylsulfonyl, aminosulfonyl, alkylsulfinyl, sulfonamido or sulfonyl;

and $R^1$ and $R^3$ may optionally be taken together to form —$(CR^5R^6)_m$— where m is 2 to 6, and $R^5$ and $R^6$ are the same or different and are independently selected from hydroxy, alkoxy, cyano, H, alkyl, alkenyl, alkynyl, cycloalkyl, cycloalkylalkyl, cycloalkenyl, aryl, arylalkyl, heteroaryl, heteroarylalkyl, cycloheteroalkyl, cycloheteroalkylalkyl, alkylcarbonylamino, arylcarbonylamino, alkoxycarbonylamino, aryloxycarbonylamino, alkoxycarbonyl, aryloxycarbonyl, or alkylaminocarbonylamino, or $R^1$ and $R^4$ may optionally be taken together to form —$(CR^7R^8)_p$— where p is 3 to 6, and $R^7$ and $R^8$ are the same or different and are independently selected from hydroxy, alkoxy, cyano, H, alkyl, alkenyl, alkynyl, cycloalkyl, cycloalkylalkyl, cycloalkenyl, aryl, arylalkyl, heteroaryl, heteroarylalkyl, cycloheteroalkyl, cycloheteroalkylalkyl, alkylcarbonylamino, arylcarbonylamino, alkoxycarbonylamino, aryloxycarbonylamino, alkoxycarbonyl, aryloxycarbonyl, or alkylaminocarbonylamino, or optionally $R^1$ and $R^3$ together with

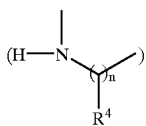

form a 5 to 7 membered ring containing a total of 2 to 4 heteroatoms selected from N, O, S, SO, or $SO_2$;

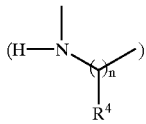

or optionally $R^1$ and $R^3$ together with form a 4 to 8 membered cycloheteroalkyl ring wherein the cycloheteroalkyl ring has an optional aryl ring fused thereto or an optional 3 to 7 membered cycloalkyl ring fused thereto;

and including pharmaceutically acceptable salts thereof, and prodrug esters thereof, and all stereoisomers thereof.

Thus, the compounds of formula I of the invention include the following structure

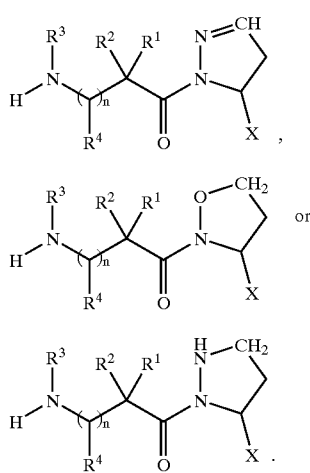

In addition, in accordance with the present invention, a method is provided for treating diabetes, especially Type II diabetes, as well as impaired glucose homeostasis, impaired glucose tolerance, infertility, polycystic ovary syndrome, growth disorders, frailty, arthritis, allograft rejection in transplantation, autoimmune diseases (such as scleroderma and multiple sclerosis), various immunomodulatory diseases (such as lupus erythematosis or psoriasis), AIDS, intestinal diseases (such as necrotizing enteritis, microvillus inclusion disease or celiac disease), inflammatory bowel syndrome, chemotherapy-induced intestinal mucosal atrophy or injury, anorexia nervosa, osteoporosis, Syndrome X, dysmetabolic syndrome, diabetic complications, hyperinsulinemia, obesity, atherosclerosis and related diseases, as well as inflammatory bowel disease(such as Crohn's disease and ulcerative colitis), wherein a therapeutically effective amount of a compound of structure I (which inhibits DP 4) is administered to a human patient in need of treatment.

The conditions, diseases, and maladies collectively referenced to as "Syndrome X" or dysmetabolic syndrome are detailed in Johannsson *J. Clin. Endocrinol. Metab.*, 82, 727–734 (1997).

In addition, in accordance with the present invention, a method is provided for treating diabetes and related diseases as defined above and hereinafter as well as any of the other disease states mentioned above, wherein a therapeutically effective amount of a combination of a compound of structure I and one, two, three or more of other types of antidiabetic agent(s) (which may be employed to treat diabetes and related diseases) and/or one, two or three or more other types of therapeutic agent(s) is administered to a human patient in need of treatment.

The term "diabetes and related diseases" refers to Type II diabetes, Type I diabetes, impaired glucose tolerance, obesity, hyperglycemia, Syndrome X, dysmetabolic syndrome, diabetic complications, and hyperinsulinemia.

The conditions, diseases and maladies collectively referred to as "diabetic complications" include retinopathy, neuropathy and nephropathy, and other known complications of diabetes.

The term "other type(s) of therapeutic agents" as employed herein refers to one or more antidiabetic agents (other than DP4 inhibitors of formula I), one or more anti-obesity agents, and/or one or more lipid-modulating agents (including anti-atherosclerosis agents), and/or one or more infertility agents, one or more agents for treating polycystic ovary syndrome, one or more agents for treating growth disorders, one or more agents for treating frailty, one or more agents for treating arthritis, one or more agents for preventing allograft rejection in transplantation, one or more agents for treating autoimmune diseases, one or more anti-AIDS agents, one or more anti-osteoporosis agents, one or more agents for treating immunomodulatory diseases, one or more agents for treating chronic inflammatory bowel disease or syndrome and/or one or more agents for treating anorexia nervosa.

The term "lipid-modulating" agent as employed herein refers to agents which lower LDL and/or raise HDL and/or lower triglycerides and/or lower total cholesterol and/or other known mechanisms for therapeutically treating lipid disorders.

In the above methods of the invention, the compound of structure I will be employed in a weight ratio to the antidiabetic agent or other type therapeutic agent (depending upon its mode of operation) within the range from about 0.01:1 to about 500:1, preferably from about 0.1:1 to about 100:1, more preferably from about 0.2:1 to about 10:1.

Preferred are compounds of formula I wherein $R^3$ is H or alkyl, $R^1$ is H, alkyl, cycloalkyl or bicycloalkyl, $R^2$ is H or alkyl, n is 0, X is CN.

Most preferred are preferred compounds of formula I as described above where X is

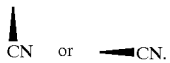

Thus, preferred compounds of formula I of the invention will include the moiety

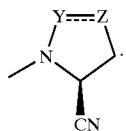

Particularly preferred are the following compounds

A) 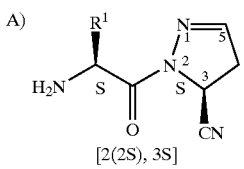

[2(2S), 3S]

wherein $R^1$ is alkyl, cycloalkyl or bicycloalkyl;

B) 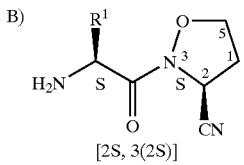

[2S, 3(2S)]

wherein $R^1$ is alkyl, cycloalkyl or bicycloalkyl.

DETAILED DESCRIPTION OF THE INVENTION

Compounds of the structure I may be generated by the methods as shown in the following reaction schemes and the description thereof.

Referring to Reaction Scheme 1, compound 1, where $X^1$ is H or $CO_2R^9$ and Y is N and Z is CH (Y and Z form a double bond) or Y is O and Z is $CH_2$ (Y and Z form a single bond) as set out below, may be generated by methods as described herein or in the literature (for example see Carreira et al, J. Am. Chem. Soc.,1997, 119, pp. 8379–8380, Henke et al, Ger. Offen. DE 3643012, Vasella, et al, Helv. Chim. Acta, 1983, 66, pp.1241–1252). Amine 1 may be coupled to various protected α- or β-amino acids such as 2 (where $PG_1$ is a common amine protecting group such as Boc, Cbz, or FMOC) using standard peptide coupling conditions (e.g. EDAC/HOAT, i-BuCOCOCl/TEA, PyBop/ NMM) to afford the corresponding dipeptide 3. Removal of the $PG_1$ group by conventional methods (e.g. (1) TFA or HCl when $PG_1$ is Boc, or (2) $H_2$/Pd/C, TMSI when $PG_1$ is Cbz, or (3) $Et_2NH$ when $PG_1$ is (FMOC) provides compound Ia of the invention where X=H.

In the case where $X^1=CO_2R^9$ (where $R^9$ is alkyl, cycloalkyl or aralkyl groups such as methyl, ethyl, t-butyl, or benzyl), the ester may be hydrolyzed under a variety of conditions, for example with aqueous NaOH in a suitable solvent such as methanol, THF, or dioxane, to provide the acid 4. Conversion of the acid group to the primary carboxamide, affording 5, may be effected by activation of the acid group (e.g. employing i-BuOCOCl/TEA or EDAC) followed by treatment with $NH_3$ or an ammonia equivalent in a solvent such as dioxane, ether, or methanol. The amide functionality may be converted to the nitrile group by a variety of standard conditions (e.g. $POCl_3$/pyridine/ imidazole or cyanuric chloride/DMF) to give 6. Finally, removal of the $PG_1$ protecting group similar to above provides compound of the invention Ib.

Similarly, referring to Reaction Scheme 2, compound 1, where $X^1$ is H or $CO_2R^9$ and Y is N–$PG^1$ ($PG^1$ is described above) and Z is $CH_2$ (Y and Z are a single bond)as set out below, may be generated by methods as described in the literature (for example see Carreira et al, J. Am. Chem. Soc.,1997, 119, pp. 8379–8380). The remaining chemistry, resulting in Ia and Ib is described as set forth above.

In a similar sequence (Scheme 3), where $X^1=CON(SO_2R^9)R^{10}$ (where $R^9$ is as described above and $R^{10}$ is alkyl, aryl, aralkyl or may be included in $R^9$ as part of a cycloalkyl or bicycloalkyl function), compound 1 may undergo ammonolysis to give amide 7, which may be subject to standard peptide coupling conditions to afford 5, an intermediate in the synthesis of Ib.

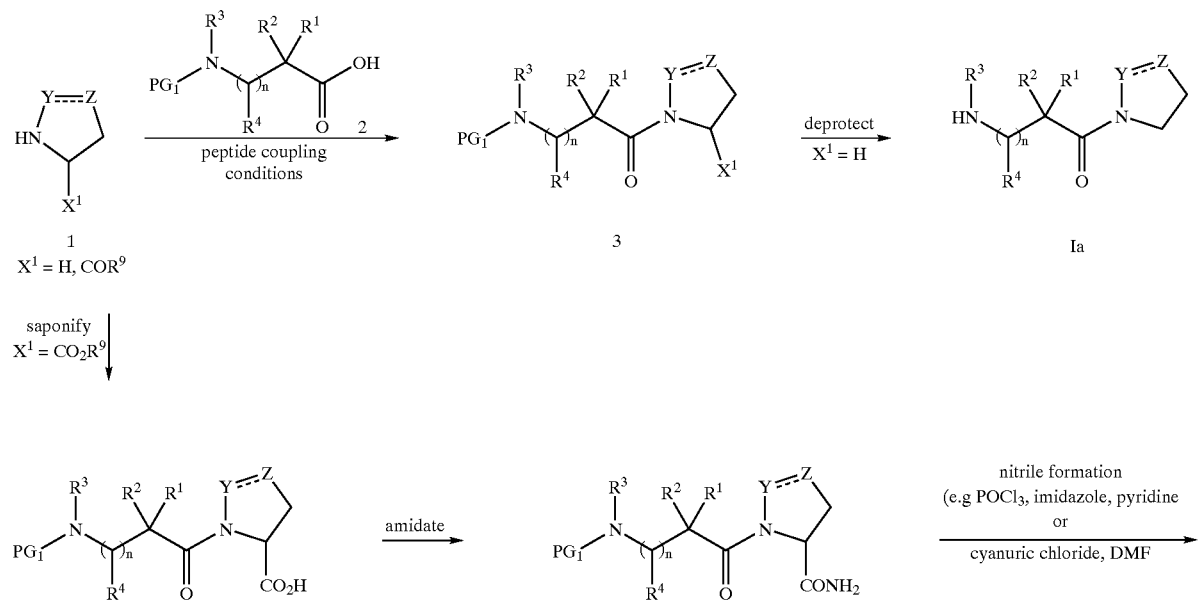

Scheme 1

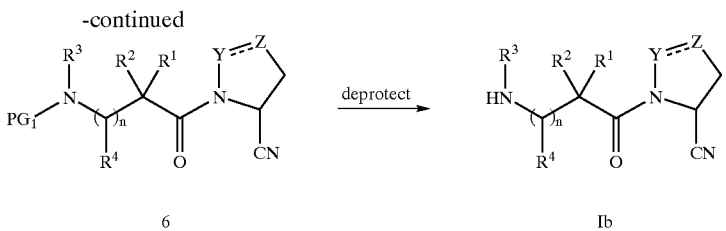

Scheme 2

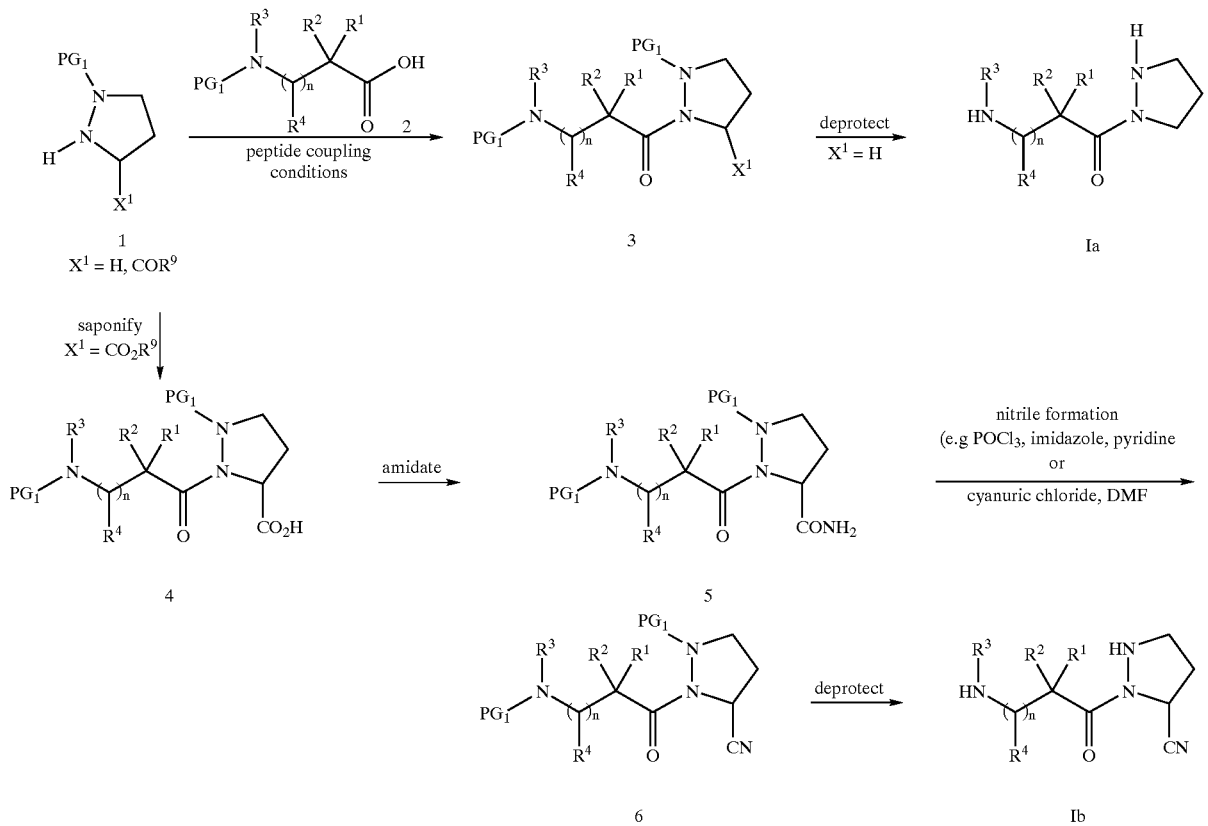

Scheme 3

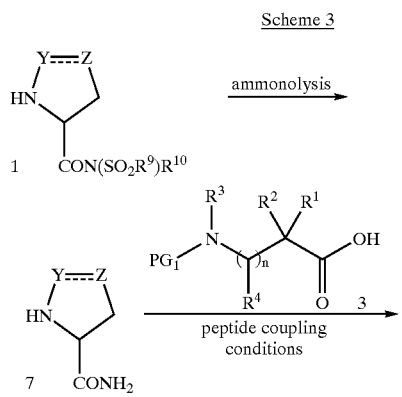

hydrocarbons, containing 1 to 20 carbons, preferably 1 to 10 carbons, more preferably 1 to 8 carbons, in the normal chain, such as methyl, ethyl, propyl, isopropyl, butyl, t-butyl, isobutyl, pentyl, hexyl, isohexyl, heptyl, 4,4-dimethylpentyl, octyl, 2,2,4-trimethyl-pentyl, nonyl, decyl, undecyl, dodecyl, the various branched chain isomers thereof, and the like as well as such groups including 1 to 4 substituents such as halo, for example F, Br, Cl or I or $CF_3$, alkyl, alkoxy, aryl, aryloxy, aryl(aryl) or diaryl, arylalkyl, arylalkyloxy, alkenyl, cycloalkyl, cycloalkylalkyl, cycloalkylalkyloxy, amino, hydroxy, hydroxyalkyl, acyl, heteroaryl, heteroaryloxy, heteroarylalkyl, heteroarylalkoxy, aryloxyalkyl, alkylthio, arylalkylthio, aryloxyaryl, alkylamido, alkanoylamino, arylcarbonylamino, nitro, cyano, thiol, haloalkyl, trihaloalkyl and/or alkylthio.

Unless otherwise indicated, the term "cycloalkyl" as employed herein alone or as part of another group includes saturated or partially unsaturated (containing 1 or 2 double bonds) cyclic hydrocarbon groups containing 1 to 3 rings, including monocyclic alkyl, bicyclic alkyl (or bicycloalkyl)

Unless otherwise indicated, the term "lower alkyl", "alkyl" or "alk" as employed herein alone or as part of another group includes both straight and branched chain and tricyclic alkyl, containing a total of 3 to 20 carbons forming the ring, preferably 3 to 10 carbons, forming the ring and which may be fused to 1 or 2 aromatic rings as described for aryl, which includes cyclopropyl, cyclobutyl, cyclopentyl, cyclohexyl, cycloheptyl, cyclooctyl, cyclodecyl and cyclododecyl, cyclohexenyl,

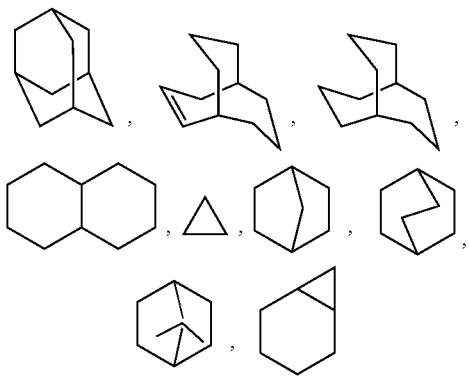

any of which groups may be optionally substituted with 1 to 4 substituents such as halogen, alkyl, alkoxy, hydroxy, aryl, aryloxy, arylalkyl, cycloalkyl, alkylamido, alkanoylamino, oxo, acyl, arylcarbonylamino, amino, nitro, cyano, thiol and/or alkylthio and/or any of the substituents for alkyl.

The term "cycloalkenyl" as employed herein alone or as part of another group refers to cyclic hydrocarbons containing 3 to 12 carbons, preferably 5 to 10 carbons and 1 or 2 double bonds. Exemplary cycloalkenyl groups include cyclopentenyl, cyclohexenyl, cycloheptenyl, cyclooctenyl, cyclohexadienyl, and cycloheptadienyl, which may be optionally substituted as defined for cycloalkyl.

The term "cycloalkylene" as employed herein refers to a "cycloalkyl" group which includes free bonds and thus is a linking group such as

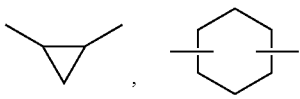

and the like, and may optionally be substituted as defined above for "cycloalkyl".

The term "alkanoyl" as used herein alone or as part of another group refers to alkyl linked to a carbonyl group.

Unless otherwise indicated, the term "lower alkenyl" or "alkenyl" as used herein by itself or as part of another group refers to straight or branched chain radicals of 2 to 20 carbons, preferably 2 to 12 carbons, and more preferably 1 to 8 carbons in the normal chain, which include one to six double bonds in the normal chain, such as vinyl, 2-propenyl, 3-butenyl, 2-butenyl, 4-pentenyl, 3-pentenyl, 2-hexenyl, 3-hexenyl, 2-heptenyl, 3-heptenyl, 4-heptenyl, 3-octenyl, 3-nonenyl, 4-decenyl, 3-undecenyl, 4-dodecenyl, 4,8,12-tetradecatrienyl, and the like, and which may be optionally substituted with 1 to 4 substituents, namely, halogen, haloalkyl, alkyl, alkoxy, alkenyl, alkynyl, aryl, arylalkyl, cycloalkyl, amino, hydroxy, heteroaryl, cycloheteroalkyl, alkanoylamino, alkylamido, arylcarbonylamino, nitro, cyano, thiol, alkylthio and/or any of the alkyl substituents set out herein.

Unless otherwise indicated, the term "lower alkynyl" or "alkynyl" as used herein by itself or as part of another group refers to straight or branched chain radicals of 2 to 20 carbons, preferably 2 to 12 carbons and more preferably 2 to 8 carbons in the normal chain, which include one triple bond in the normal chain, such as 2-propynyl, 3-butynyl, 2-butynyl, 4-pentynyl, 3-pentynyl, 2-hexynyl, 3-hexynyl, 2-heptynyl, 3-heptynyl, 4-heptynyl, 3-octynyl, 3-nonynyl, 4-decynyl, 3-undecynyl, 4-dodecynyl and the like, and which may be optionally substituted with 1 to 4 substituents, namely, halogen, haloalkyl, alkyl, alkoxy, alkenyl, alkynyl, aryl, arylalkyl, cycloalkyl, amino, heteroaryl, cycloheteroalkyl, hydroxy, alkanoylamino, alkylamido, arylcarbonylamino, nitro, cyano, thiol, and/or alkylthio, and/or any of the alkyl substituents set out herein.

The terms "arylalkenyl" and "arylalkynyl" as used alone or as part of another group refer to alkenyl and alkynyl groups as described above having an aryl substituent.

Where alkyl groups as defined above have single bonds for attachment to other groups at two different carbon atoms, they are termed "alkylene" groups and may optionally be substituted as defined above for "alkyl".

Where alkenyl groups as defined above and alkynyl groups as defined above, respectively, have single bonds for attachment at two different carbon atoms, they are termed "alkenylene groups" and "alkynylene groups", respectively, and may optionally be substituted as defined above for "alkenyl" and "alkynyl".

The term "halogen" or "halo" as used herein alone or as part of another group refers to chlorine, bromine, fluorine, and iodine as well as $CF_3$, with chlorine or fluorine being preferred.

The term "metal ion" refers to alkali metal ions such as sodium, potassium or lithium and alkaline earth metal ions such as magnesium and calcium, as well as zinc and aluminum.

Unless otherwise indicated, the term "aryl" as employed herein alone or as part of another group refers to monocyclic and bicyclic aromatic groups containing 6 to 10 carbons in the ring portion (such as phenyl or naphthyl including 1-naphthyl and 2-naphthyl) and may optionally include one to three additional rings fused to a carbocyclic ring or a heterocyclic ring (such as aryl, cycloalkyl, heteroaryl or cycloheteroalkyl rings for example

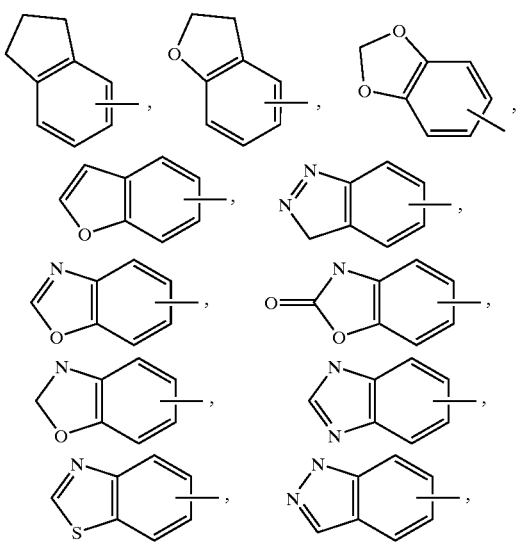

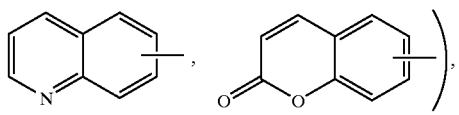

and may be optionally substituted through available carbon atoms with 1, 2, or 3 groups selected from hydrogen, halo, haloalkyl, alkyl, haloalkyl, alkoxy, haloalkoxy, alkenyl, trifluoromethyl, trifluoromethoxy, alkynyl, cycloalkyl-alkyl, cycloheteroalkyl, cycloheteroalkylalkyl, aryl, heteroaryl, arylalkyl, aryloxy, aryloxyalkyl, arylalkoxy, arylthio, arylazo, heteroarylalkyl, heteroarylalkenyl, heteroarylheteroaryl, heteroaryloxy, hydroxy, nitro, cyano, amino, substituted amino wherein the amino includes 1 or 2 substituents (which are alkyl, aryl or any of the other aryl compounds mentioned in the definitions), thiol, alkylthio, arylthio, heteroarylthio, arylthioalkyl, alkoxyarylthio, alkylcarbonyl, arylcarbonyl, alkylaminocarbonyl, arylaminocarbonyl, alkoxycarbonyl, aminocarbonyl, alkylcarbonyloxy, arylcarbonyloxy, alkylcarbonylamino, arylcarbonylamino, arylsulfinyl, arylsulfinylalkyl, arylsulfonylamino or arylsulfonaminocarbonyl and/or any of the alkyl substituents set out herein.

Unless otherwise indicated, the term "lower alkoxy", "alkoxy", "aryloxy" or "aralkoxy" as employed herein alone or as part of another group includes any of the above alkyl, aralkyl or aryl groups linked to an oxygen atom.

Unless otherwise indicated, the term "substituted amino" as employed herein alone or as part of another group refers to amino substituted with one or two substituents, which may be the same or different, such as alkyl, aryl, arylalkyl, heteroaryl, heteroarylalkyl, cycloheteroalkyl, cycloheteroalkylalkyl, cycloalkyl, cycloalkylalkyl, haloalkyl, hydroxyalkyl, alkoxyalkyl or thioalkyl. These substituents may be further substituted with a carboxylic acid and/or any of the $R^1$ groups or substituents for $R^1$ as set out above. In addition, the amino substituents may be taken together with the nitrogen atom to which they are attached to form 1-pyrrolidinyl, 1-piperidinyl, 1-azepinyl, 4-morpholinyl, 4-thiamorpholinyl, 1-piperazinyl, 4-alkyl-1-piperazinyl, 4-arylalkyl-1-piperazinyl, 4-diarylalkyl-1-piperazinyl, 1-pyrrolidinyl, 1-piperidinyl, or 1-azepinyl, optionally substituted with alkyl, alkoxy, alkylthio, halo, trifluoromethyl or hydroxy.

Unless otherwise indicated, the term "lower alkylthio", alkylthio", "arylthio" or "aralkylthio" as employed herein alone or as part of another group includes any of the above alkyl, aralkyl or aryl groups linked to a sulfur atom.

Unless otherwise indicated, the term "lower alkylamino", "alkylamino", "arylamino", or "arylalkylamino" as employed herein alone or as part of another group includes any of the above alkyl, aryl or arylalkyl groups linked to a nitrogen atom.

Unless otherwise indicated, the term "acyl" as employed herein by itself or part of another group, as defined herein, refers to an organic radical linked to a carbonyl

group; examples of acyl groups include any of the $R^1$ groups attached to a carbonyl, such as alkanoyl, alkenoyl, aroyl, aralkanoyl, heteroaroyl, cycloalkanoyl, cycloheteroalkanoyl and the like.

Unless otherwise indicated, the term "cycloheteroalkyl" as used herein alone or as part of another group refers to a 5-, 6- or 7-membered saturated or partially unsaturated ring which includes 1 to 2 hetero atoms such as nitrogen, oxygen and/or sulfur, linked through a carbon atom or a heteroatom, where possible, optionally via the linker $(CH_2)_r$ (where r is 1, 2 or 3), such as

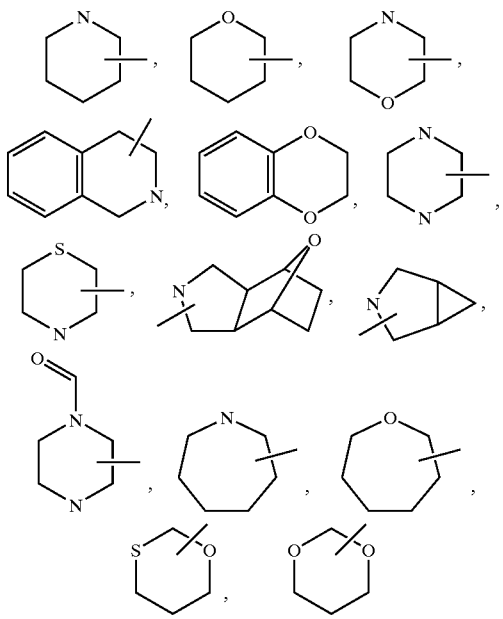

and the like. The above groups may include 1 to 4 substituents such as alkyl, halo, oxo and/or any of of the alkyl substituents set out herein. In addition, any of the cycloheteroalkyl rings can be fused to a cycloalkyl, aryl, heteroaryl or cycloheteroalkyl ring.

Unless otherwise indicated, the term "heteroaryl" as used herein alone or as part of another group refers to a 5- or 6-membered aromatic ring which includes 1, 2, 3 or 4 hetero atoms such as nitrogen, oxygen or sulfur,and such rings fused to an aryl, cycloalkyl, heteroaryl or cycloheteroalkyl ring (e.g. benzothiophenyl, indolyl), and includes possible N-oxides. The heteroaryl group may optionally include 1 to 4 substituents such as any of the substituents set out above for alkyl. Examples of heteroaryl groups include the following:

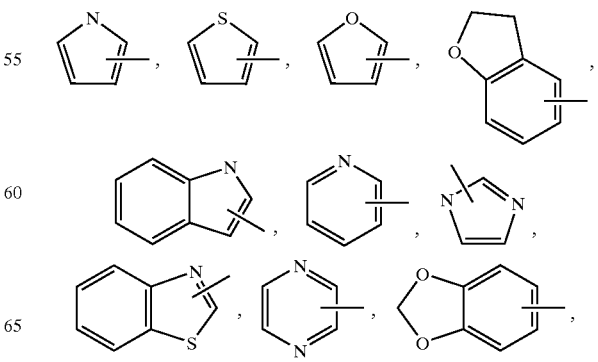

-continued

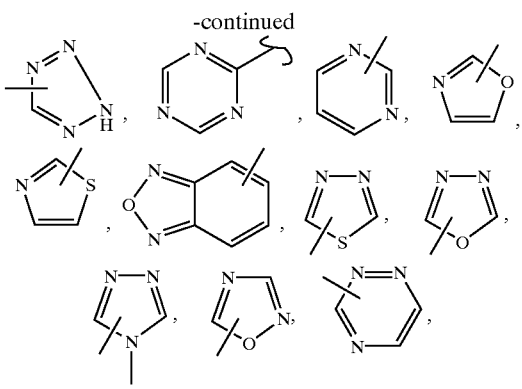

and the like.

The term "cycloheteroalkylalkyl" as used herein alone or as part of another group refers to cycloheteroalkyl groups as defined above linked through a C atom or heteroatom to a $(CH_2)_r$ chain.

The term "heteroarylalkyl" or "heteroarylalkenyl" as used herein alone or as part of another group refers to a heteroaryl group as defined above linked through a C atom or heteroatom to a —$(CH^2)_r$— chain, alkylene or alkenylene as defined above.

The term "polyhaloalkyl" as used herein refers to an "alkyl" group as defined above which includes from 2 to 9, preferably from 2 to 5, halo substituents, such as F or Cl, preferably F, such as $CF_3CH_2$, $CF_3$ or $CF_3CF_2CH_2$.

The term "polyhaloalkoxy" as used herein refers to an "alkoxy" or "alkyloxy" group as defined above which includes from 2 to 9, preferably from 2 to 5, halo substituents, such as F or Cl, preferably F, such as $CF_3CH_2O$, $CF_3O$ or $CF_3CF_2CH_2O$.

All stereoisomers of the compounds of the instant invention are contemplated, either in admixture or in pure or substantially pure form. The compounds of the present invention can have asymmetric centers at any of the carbon atoms including any one or the R substituents. Consequently, compounds of formula I can exist in enantiomeric or diastereomeric forms or in mixtures thereof. The processes for preparation can utilize racemates, enantiomers or diastereomers as starting materials. When diastereomeric or enantiomeric products are prepared, they can be separated by conventional methods for example, chromatographic or fractional crystallization.

Where desired, the compounds of structure I may be used in combination with one or more other types of antidiabetic agents (employed to treat diabetes and related diseases) and/or one or more other types of therapeutic agents which may be administered orally in the same dosage form, in a separate oral dosage form or by injection.

The other type of antidiabetic agent which may be optionally employed in combination with the DP4 inhibitor of formula I may be 1,2,3 or more antidiabetic agents or antihyperglycemic agents including insulin secretagogues or insulin sensitizers, or other antidiabetic agents preferably having a mechanism of action different from DP4 inhibition and may include biguanides, sulfonyl ureas, glucosidase inhibitors, PPAR γ agonists, such as thiazolidinediones, SGLT2 inhibitors, PPAR α/γ dual agonists, aP2 inhibitors, glycogen phosphorylase inhibitors, advanced glycosylation end (AGE) products inhibitors, and/or meglitinides, as well as insulin, and/or glucagon-like peptide-1 (GLP-1) or mimetics thereof.

It is believed that the use of the compounds of structure I in combination with 1, 2, 3 or more other antidiabetic agents produces antihyperglycemic results greater than that possible from each of these medicaments alone and greater than the combined additive anti-hyperglycemic effects produced by these medicaments.

The other antidiabetic agent may be an oral antihyperglycemic agent preferably a biguanide such as metformin or phenformin or salts thereof, preferably metformin HCl.

Where the other antidiabetic agent is a biguanide, the compounds of structure I will be employed in a weight ratio to biguanide within the range from about 0.01:1 to about 100:1, preferably from about 0.1:1 to about 5:1.

The other antidiabetic agent may also preferably be a sulfonyl urea such as glyburide (also known as glibenclamide), glimepiride (disclosed in U.S. Pat. No. 4,379,785), glipizide, gliclazide or chlorpropamide, other known sulfonylureas or other antihyperglycemic agents which act on the ATP-dependent channel of the β-cells, with glyburide and glipizide being preferred, which may be administered in the same or in separate oral dosage forms.

The compounds of structure I will be employed in a weight ratio to the sulfonyl urea in the range from about 0.01:1 to about 100:1, preferably from about 0.05:1 to about 5:1.

The oral antidiabetic agent may also be a glucosidase inhibitor such as acarbose (disclosed in U.S. Pat. No. 4,904,769) or miglitol (disclosed in U.S. Pat. No. 4,639,436), which may be administered in the same or in a separate oral dosage forms.

The compounds of structure I will be employed in a weight ratio to the glucosidase inhibitor within the range from about 0.01:1 to about 100:1, preferably from about 0.2:1 to about 50:1.

The compounds of structure I may be employed in combination with a PPAR γ agonist such as a thiazolidinedione oral anti-diabetic agent or other insulin sensitizers (which has an insulin sensitivity effect in NIDDM patients) such as troglitazone (Warner-Lambert's Rezulin®, disclosed in U.S. Pat. No. 4,572,912), rosiglitazone (SKB), pioglitazone (Takeda), Mitsubishi's MCC-555 (disclosed in U.S. Pat. No. 5,594,016), Glaxo-Wellcome's GL-262570, englitazone (CP-68722, Pfizer) or darglitazone (CP-86325, Pfizer, isaglitazone (MIT/J&J), JTT-501 (JPNT/P&U), L-895645 (Merck), R-119702 (Sankyo/WL), NN-2344 (Dr. Reddy/NN), or YM-440 (Yamanouchi), preferably rosiglitazone and pioglitazone.

The compounds of structure I will be employed in a weight ratio to the thiazolidinedione in an amount within the range from about 0.01:1 to about 100:1, preferably from about 0.1:1 to about 10:1.

The sulfonyl urea and thiazolidinedione in amounts of less than about 150 mg oral antidiabetic agent may be incorporated in a single tablet with the compounds of structure I.

The compounds of structure I may also be employed in combination with a antihyperglycemic agent such as insulin or with glucagon-like peptide-1 (GLP-1) such as GLP-1 (1–36) amide, GLP-1(7–36) amide, GLP-1(7–37) (as disclosed in U.S. Pat. No. 5,614,492 to Habener, disclosure of which is incorporated herein by reference), or a GLP-1 mimic such as AC2993 or Exendin-4 (Amylin) and LY-315902 or LY-307167 (Lilly) and NN2211 (Novo-Nordisk), which may be administered via injection, intranasal, or by transdermal or buccal devices.

Where present, metformin, the sulfonyl ureas, such as glyburide, glimepiride, glipyride, glipizide, chlorpropamide and gliclazide and the glucosidase inhibitors acarbose or miglitol or insulin (injectable, pulmonary, buccal, or oral)

may be employed in formulations as described above and in amounts and dosing as indicated in the Physician's Desk Reference (PDR).

Where present, metformin or salt thereof may be employed in amounts within the range from about 500 to about 2000 mg per day which may be administered in single or divided doses one to four times daily.

Where present, the thiazolidinedione anti-diabetic agent may be employed in amounts within the range from about 0.01 to about 2000 mg/day which may be administered in single or divided doses one to four times per day.

Where present insulin may be employed in formulations, amounts and dosing as indicated by the Physician's Desk Reference.

Where present GLP-1 peptides may be administered in oral buccal formulations, by nasal administration (for example inhalation spray) or parenterally as described in U.S. Pat. Nos. 5,346,701 (TheraTech), 5,614,492 and 5,631,224 which are incorporated herein by reference.

The other antidiabetic agent may also be a PPAR α/γ dual agonist such as AR-HO39242 (Astra/Zeneca), GW-409544 (Glaxo-Wellcome), KRP297 (Kyorin Merck) as well as those disclosed by Murakami et al, "A Novel Insulin Sensitizer Acts As a Coligand for Peroxisome Proliferation—Activated Receptor Alpha (PPAR alpha) and PPAR gamma. Effect on PPAR alpha Activation on Abnormal Lipid Metabolism in Liver of Zucker Fatty Rats", Diabetes 47, 1841–1847 (1998), and in U.S. application Ser. No. 09/664,598, filed Sep. 18, 2000, (attorney file LA29NP) the disclosure of which is incorporated herein by reference, employing dosages as set out therein, which compounds designated as preferred are preferred for use herein.

The other antidiabetic agent may be an SGLT2 inhibitor such as disclosed in U.S. application Ser. No. 09/679,027, filed Oct. 4, 2000 (attorney file LA49NP), which is incorporated herein by reference, employing dosages as set out herein. Preferred are the compounds designated as preferred in the above application.

The other antidiabetic agent which may be optionally employed in combination with the DP4 inhibitor of formula I may be an aP2 inhibitor such as disclosed in U.S. application Ser. No. 09/391,053, filed Sep. 7, 1999, and U.S. application Ser. No. 09/519,079, filed Mar. 6, 2000 (attorney file LA27NP), which is incorporated herein by reference, employing dosages as set out herein. Preferred are the compounds designated as preferred in the above application.

The other antidiabetic agent which may be optionally employed in combination with the DP4 inhibitor of formula I may be a glycogen phosphorylase inhibitor such as disclosed in WO 96/39384, WO 96/39385, EP 978279, WO 2000/47206, WO 99/43663, and U.S. Pat. Nos. 5,952,322 and 5,998,463, WO 99/26659 and EP 1041068.

The meglitinide which may optionally be employed in combination with the compound of formula I of the invention may be repaglinide, nateglinide (Novartis) or KAD1229 (PF/Kissei), with repaglinide being preferred.

The DP4 inhibitor of formula I will be employed in a weight ratio to the meglitinide, PPAR γ agonist, PPAR α/γ dual agonist, SGLT2 inhibitor, aP2 inhibitor, or glycogen phosphorylase inhibitor within the range from about 0.01:1 to about 100:1, preferably from about 0.1:1 to about 10:1.

The hypolipidemic agent or lipid-modulating agent which may be optionally employed in combination with the compounds of formula I of the invention may include 1,2,3 or more MTP inhibitors, HMG CoA reductase inhibitors, squalene synthetase inhibitors, fibric acid derivatives, ACAT inhibitors, lipoxygenase inhibitors, cholesterol absorption inhibitors, ileal Na+/bile acid cotransporter inhibitors, upregulators of LDL receptor activity, cholesteryl ester transfer protein inhibitors, bile acid sequestrants, and/or nicotinic acid and derivatives thereof.

MTP inhibitors employed herein include MTP inhibitors disclosed in U.S. Pat. Nos. 5,595,872, 5,739,135, 5,712,279, 5,760,246, 5,827,875, 5,885,983 and U.S. application Ser. No. 09/175,180 filed Oct. 20, 1998, now U.S. Pat. No. 5,962,440. Preferred are each of the preferred MTP inhibitors disclosed in each of the above patents and applications.

All of the above U.S. Patents and applications are incorporated herein by reference.

Most preferred MTP inhibitors to be employed in accordance with the present invention include preferred MTP inhibitors as set out in U.S. Pat. Nos. 5,739,135 and 5,712,279, and U.S. Pat. No. 5,760,246 as well as implitapide (Bayer).

The most preferred MTP inhibitor is 9-[4-[4-[[2-(2,2,2-Trifluoroethoxy)benzoyl]amino]-1-piperidinyl]butyl]-N-(2,2,2-trifluoroethyl)-9H-fluorene-9-carboxamide

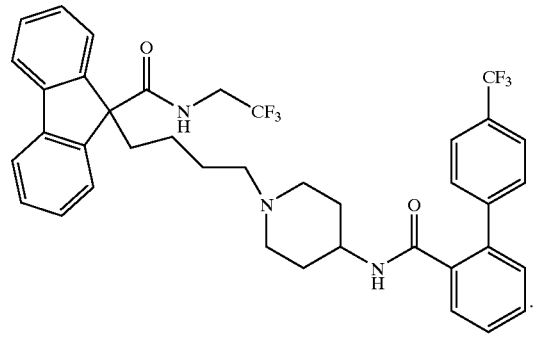

The hypolipidemic agent may be an HMG CoA reductase inhibitor which includes, but is not limited to, mevastatin and related compounds as disclosed in U.S. Pat. No. 3,983,140, lovastatin (mevinolin) and related compounds as disclosed in U.S. Pat. No. 4,231,938, pravastatin and related compounds such as disclosed in U.S. Pat. No. 4,346,227, simvastatin and related compounds as disclosed in U.S. Pat. Nos. 4,448,784 and 4,450,171. Other HMG CoA reductase inhibitors which may be employed herein include, but are not limited to, fluvastatin, disclosed in U.S. Pat. No. 5,354,772, cerivastatin disclosed in U.S. Pat. Nos. 5,006,530 and 5,177,080, atorvastatin disclosed in U.S. Pat. Nos. 4,681,893, 5,273,995, 5,385,929 and 5,686,104, atavastatin (Nissan/Sankyo's nisvastatin (NK-104)) disclosed in U.S. Pat. No. 5,011,930, Shionogi-Astra/Zeneca visastatin (ZD-4522) disclosed in U.S. Pat. No. 5,260,440.

The squalene synthetase inhibitors suitable for use herein include, but are not limited to, α-phosphono-sulfonates disclosed in U.S. Pat. No. 5,712,396, those disclosed by Biller et al, J. Med. Chem., 1988, Vol. 31, No. 10, pp 1869–1871, including isoprenoid (phosphinyl-methyl) phosphonates as well as other known squalene synthetase inhibitors, for example, as disclosed in U.S. Pat. No. 4,871,721 and 4,924,024 and in Biller, S. A., Neuenschwander, K., Ponpipom, M. M., and Poulter, C. D., Current Pharmaceutical Design, 2, 1–40 (1996).

In addition, other squalene synthetase inhibitors suitable for use herein include the terpenoid pyrophosphates disclosed by P. Ortiz de Montellano et al, J. Med. Chem., 1977, 20, 243–249, the farnesyl diphosphate analog A and presqualene pyrophosphate (PSQ-PP) analogs as disclosed by Corey and Volante, J. Am. Chem. Soc., 1976, 98, 1291–1293, phosphinylphosphonates reported by McClard, R. W. et al, J.A.C.S., 1987, 109, 5544 and cyclopropanes reported by Capson, T. L., PhD dissertation, June, 1987, Dept. Med. Chem. U of Utah, Abstract, Table of Contents, pp 16, 17, 40–43, 48–51, Summary.

Other hypolipidemic agents suitable for use herein include, but are not limited to, fibric acid derivatives, such as fenofibrate, gemfibrozil, clofibrate, bezafibrate, ciprofibrate, clinofibrate and the like, probucol, and related compounds as disclosed in U.S. Pat. No. 3,674,836, probucol and gemfibrozil being preferred, bile acid sequestrants such as cholestyramine, colestipol and DEAE-Sephadex (Secholex®, Policexide®), as well as lipostabil (Rhone-Poulenc), Eisai E-5050 (an N-substituted ethanolamine derivative), imanixil (HOE-402), tetrahydrolipstatin (THL), istigmastanylphos-phorylcholine (SPC, Roche), aminocyclodextrin (Tanabe Seiyoku), Ajinomoto AJ-814 (azulene derivative), melinamide (Sumitomo), Sandoz 58-035, American Cyanamid CL-277,082 and CL-283,546 (disubstituted urea derivatives), nicotinic acid, acipimox, acifran, neomycin, p-aminosalicylic acid, aspirin, poly (diallylmethylamine) derivatives such as disclosed in U.S. Pat. No. 4,759,923, quaternary amine poly (diallyldimethylammonium chloride) and ionenes such as disclosed in U.S. Pat. No. 4,027,009, and other known serum cholesterol lowering agents.

The other hypolipidemic agent may be an ACAT inhibitor such as disclosed in, Drugs of the Future 24, 9–15 (1999), (Avasimibe); "The ACAT inhibitor, Cl-1011 is effective in the prevention and regression of aortic fatty streak area in hamsters", Nicolosi et al, Atherosclerosis (Shannon, Irel). (1998), 137(1), 77–85; "The pharmacological profile of FCE 27677: a novel ACAT inhibitor with potent hypolipidemic activity mediated by selective suppression of the hepatic secretion of ApoB100-containing lipoprotein", Ghiselli, Giancarlo, Cardiovasc. Drug Rev. (1998), 16(1), 16–30; "RP 73163: a bioavailable alkylsulfinyl-diphenylimidazole ACAT inhibitor", Smith, C., et al, Bioorg. Med. Chem. Lett. (1996), 6(1), 47–50; "ACAT inhibitors: physiologic mechanisms for hypolipidemic and anti-atherosclerotic activities in experimental animals", Krause et al, Editor(s): Ruffolo, Robert R., Jr.; Hollinger, Mannfred A., Inflammation: Mediators Pathways (1995), 173–98, Publisher: CRC, Boca Raton, Fla.; "ACAT inhibitors: potential anti-atherosclerotic agents", Sliskovic et al, Curr. Med. Chem. (1994), 1(3), 204–25; "Inhibitors of acyl-CoA:cholesterol O-acyl transferase (ACAT) as hypocholesterolemic agents. 6. The first water-soluble ACAT inhibitor with lipid-regulating activity. Inhibitors of acyl-CoA:cholesterol acyltransferase (ACAT). 7. Development of a series of substituted N-phenyl-N'-[(1-phenylcyclopentyl)methyl]ureas with enhanced hypocholesterolemic activity", Stout et al, Chemtracts: Org. Chem. (1995), 8(6), 359–62, or TS-962 (Taisho Pharmaceutical Co. Ltd).

The hypolipidemic agent may be an upregulator of LD2 receptor activity such as MD-700 (Taisho Pharmaceutical Co. Ltd) and LY295427 (Eli Lilly).

The hypolipidemic agent may be a cholesterol absorption inhibitor preferably Schering-Plough's SCH48461 as well as those disclosed in Atherosclerosis 115, 45–63 (1995) and J. Med. Chem. 41, 973 (1998).

The hypolipidemic agent may be an ileal $Na^+$/bile acid cotransporter inhibitor such as disclosed in Drugs of the Future, 24, 425–430 (1999).

The lipid-modulating agent may be a cholesteryl ester transfer protein (CETP) inhibitor such as Pfizer's CP 529, 414 (WO/0038722 and EP 818448) and Pharmacia's SC-744 and SC-795.

Preferred hypolipidemic agents are pravastatin, lovastatin, simvastatin, atorvastatin, fluvastatin, cerivastatin, itavastatin and ZD-4522.

The above-mentioned U.S. patents are incorporated herein by reference. The amounts and dosages employed will be as indicated in the Physician's Desk Reference and/or in the patents set out above.

The compounds of formula I of the invention will be employed in a weight ratio to the hypolipidemic agent (were present), within the range from about 500:1 to about 1:500, preferably from about 100:1 to about 1:100.

The dose administered must be carefully adjusted according to age, weight and condition of the patient, as well as the route of administration, dosage form and regimen and the desired result.

The dosages and formulations for the hypolipidemic agent will be as disclosed in the various patents and applications discussed above.

The dosages and formulations for the other hypolipidemic agent to be employed, where applicable, will be as set out in the latest edition of the Physicians' Desk Reference.

For oral administration, a satisfactory result may be obtained employing the MTP inhibitor in an amount within the range of from about 0.01 mg/kg to about 500 mg and preferably from about 0.1 mg to about 100 mg, one to four times daily.

A preferred oral dosage form, such as tablets or capsules, will contain the MTP inhibitor in an amount of from about 1 to about 500 mg, preferably from about 2 to about 400 mg, and more preferably from about 5 to about 250 mg, one to four times daily.

For oral administration, a satisfactory result may be obtained employing an HMG CoA reductase inhibitor, for example, pravastatin, lovastatin, simvastatin, atorvastatin, fluvastatin or cerivastatin in dosages employed as indicated in the Physician's Desk Reference, such as in an amount within the range of from about 1 to 2000 mg, and preferably from about 4 to about 200 mg.

The squalene synthetase inhibitor may be employed in dosages in an amount within the range of from about 10 mg to about 2000 mg and preferably from about 25 mg to about 200 mg.

A preferred oral dosage form, such as tablets or capsules, will contain the HMG CoA reductase inhibitor in an amount from about 0.1 to about 100 mg, preferably from about 5 to about 80 mg, and more preferably from about 10 to about 40 mg.

A preferred oral dosage form, such as tablets or capsules will contain the squalene synthetase inhibitor in an amount of from about 10 to about 500 mg, preferably from about 25 to about 200 mg.

The other hypolipidemic agent may also be a lipoxygenase inhibitor including a 15-lipoxygenase (15-LO) inhibitor such as benzimidazole derivatives as disclosed in WO 97/12615, 15-LO inhibitors as disclosed in WO 97/12613, isothiazolones as disclosed in WO 96/38144, and 15-LO inhibitors as disclosed by Sendobry et al "Attenuation of diet-induced atherosclerosis in rabbits with a highly selective 15-lipoxygenase inhibitor lacking significant antioxidant properties", Brit. J. Pharmacology (1997) 120, 1199–1206, and Cornicelli et al, "15-Lipoxygenase and its Inhibition: A Novel Therapeutic Target for Vascular Disease", Current Pharmaceutical Design, 1999, 5, 11–20.

The compounds of formula I and the hypolipidemic agent may be employed together in the same oral dosage form or in separate oral dosage forms taken at the same time.

The compositions described above may be administered in the dosage forms as described above in single or divided doses of one to four times daily. It may be advisable to start a patient on a low dose combination and work up gradually to a high dose combination.

The preferred hypolipidemic agent is pravastatin, simvastatin, lovastatin, atorvastatin, fluvastatin, cerivastatin, visastatin or itavastatin.

The other type of therapeutic agent which may be optionally employed with the DP4 inhibitor of formula I may be 1, 2, 3 or more of an anti-obesity agent including a beta 3 adrenergic agonist, a lipase inhibitor, a serotonin (and dopamine) reuptake inhibitor, a thyroid receptor beta drug, an anorectic agent and/or a fatty acid oxidation upregulator.

The beta 3 adrenergic agonist which may be optionally employed in combination with a compound of formula I may be AJ9677 (Takeda/Dainippon), L750355 (Merck), or CP331648 (Pfizer) or other known beta 3 agonists as disclosed in U.S. Pat. Nos. 5,541,204, 5,770,615, 5,491,134, 5,776,983 and 5,488,064, with AJ9677, L750,355 and CP331648 being preferred.

The lipase inhibitor which may be optionally employed in combination with a compound of formula I may be orlistat or ATL-962 (Alizyme), with orlistat being preferred.

The serotonin (and dopamine) reuptake inhibitor which may be optionally employed in combination with a compound of formula I may be sibutramine or topiramate (Johnson & Johnson).

The thyroid receptor beta compound which may be optionally employed in combination with a compound of formula I may be a thyroid receptor ligand as disclosed in WO97/21993 (U. Cal SF), WO99/00353 (KaroBio) and GB98/284425 (KaroBio), with compounds of the KaroBio applications being preferred.

The anorectic agent which may be optionally employed in combination with a compound of formula I may be dexamphetamine, phentermine, phenylpropanolamine or mazindol, with dexamphetamine being preferred.

The fatty acid oxidation upregulator which may be optionally employed in combination with the compound of formula I can be famoxin (Genset).

The various anti-obesity agents described above may be employed in the same dosage form with the compound of formula I or in different dosage forms, in dosages and regimens as generally known in the art or in the PDR.

The infertility agent which may be optionally employed in combination with the DP4 inhibitor of the invention may be 1, 2, or more of clomiphene citrate (Clomid®, Aventis), bromocriptine mesylate (Parlodel®, Novartis),LHRH analogs, Lupron (TAP Pharm.), danazol, Danocrine (Sanofi), progestogens or glucocorticoids, which may be employed in amounts specified in the PDR.

The agent for polycystic ovary syndrome which may be optionally employed in combination with the DP4 inhibitor of the invention may be 1, 2, or more of gonadotropin releasing hormone (GnRH), leuprolide (Lupron®), Clomid®, Parlodel®, oral contraceptives or insulin sensitizers such as PPAR agonists, or other conventional agents for such use which may be employed in amounts specified in the PDR.

The agent for treating growth disorders and/or frailty which may be optionally employed in combination with the DP4 inhibitor of the invention may be 1, 2, or more of a growth hormone or growth hormone secretagogue such as MK-677 (Merck), CP-424,391 (Pfizer), and compounds disclosed in U.S. Ser. No. 09/506,749 filed Feb. 18, 2000 (attorney docket LA26), as well as selective androgen receptor modulators (SARMs), which is incorporated herein by reference, which may be employed in amounts specified in the PDR, where applicable.

The agent for treating arthritis which may be optionally employed in combination with the DP4 inhibitor of the invention may be 1, 2, or more of aspirin, indomethacin, ibuprofen, diclofenac sodium, naproxen, nabumetone (Relafen®, SmithKline Beecham), tolmetin sodium (Tolectin®, Ortho-McNeil), piroxicam (Feldene®, Pfizer), ketorolac tromethamine (Toradol®, Roche), celecoxib (Celebrex®, Searle), rofecoxib (Vioxx®, Merck) and the like, which may be employed in amounts specified in the PDR.

Conventional agents for preventing allograft rejection in transplantation such as cyclosporin, Sandimmune (Novartis), azathioprine, Immuran (Faro) or methotrexate may be optionally employed in combination with the DP4 inhibitor of the invention, which may be employed in amounts specified in the PDR.

Conventional agents for treating autoimmune diseases such as multiple sclerosis and immunomodulatory diseases such as lupus erythematosis, psoriasis, for example, azathioprine, Immuran, cyclophosphamide, NSAIDS such as ibuprofen, cox 2 inhibitors such as Vioxx and Celebrex, glucocorticoids and hydroxychloroquine, may be optionally employed in combination with the DP4 inhibitor of the invention, which may be employed in amounts specified in the PDR.

The AIDS agent which may be optionally employed in combination with the DP4 inhibitor of the invention may be a non-nucleoside reverse transcriptase inhibitor, a nucleoside reverse transcriptase inhibitor, a protease inhibitor and/or an AIDS adjunct anti-infective and may be 1, 2, or more of dronabinol (Marinol®, Roxane Labs), didanosine (Videx®, Bristol-Myers Squibb), megestrol acetate (Megace®, Bristol-Myers Squibb), stavudine (Zerit®, Bristol-Myers Squibb), delavirdine mesylate (Rescriptor®, Pharmacia), lamivudine/zidovudine (Combivir™, Glaxo), lamivudine (Epivir™, Glaxo), zalcitabine (Hivid®, Roche), zidovudine (Retrovir®, Glaxo), indinavir sulfate (Crixivan®, Merck), saquinavir (Fortovase™, Roche), saquinovir mesylate (Invirase®, Roche), ritonavir (Norvir®, Abbott), nelfinavir (Viracept®, Agouron).

The above anti-AIDS agents may be employed in amounts specified in the PDR.

The agent for treating inflammatory bowel disease or syndrome which may be optionally employed in combination with the DP4 inhibitor of the invention may be 1, 2, or more of sulfasalazine, salicylates, mesalamine (Asacol®, P&G) or Zelmac®, (Bristol-Myers Squibb), which may be employed in amounts specified in the PDR or otherwise known in the art.

The agent for treating osteoporosis which may be optionally employed in combination with the DP4 inhibitor of the invention may be 1, 2, or more of alendronate sodium (Fosamax®, Merck, tiludronate (Skelid®, Sanofi), etidronate disodium (Didronel®, P&G), raloxifene HCl (Evista®, Lilly), which may be employed in amounts specified in the PDR.

In carrying our the method of the invention, a pharmaceutical composition will be employed containing the compounds of structure I, with or without another antidiabetic agent and/or other type therapeutic agent, in association with a pharmaceutical vehicle or diluent. The pharmaceutical composition can be formulated employing conventional solid or liquid vehicles or diluents and pharmaceutical additives of a type appropriate to the mode of desired administration. The compounds can be administered to mammalian species including humans, monkeys, dogs, etc. by an oral route, for example, in the form of tablets, capsules, granules or powders, or they can be administered by a parenteral route in the form of injectable preparations. The dose for adults is preferably between 10 and 1,000 mg per day, which can be administered in a single dose or in the form of individual doses from 1–4 times per day.

A typical capsule for oral administration contains compounds of structure I (250 mg), lactose (75 mg) and magnesium stearate (15 mg). The mixture is passed through a 60 mesh sieve and packed into a No. 1 gelatin capsule.

A typical injectable preparation is produced by aseptically placing 250 mg of compounds of structure I into a vial, aseptically freeze-drying and sealing. For use, the contents of the vial are mixed with 2 mL of physiological saline, to produce an injectable preparation.

DP4 inhibitor activity of the compounds of the invention may be determined by use of an in vitro assay system which measures the potentiation of inhibition of DP4. Inhibition constants (Ki values) for the DP4 inhibitors of the invention may be determined by the method described below.

Purification of Porcine Dipeptidyl Peptidase IV

Porcine enzyme was purified as previously described (1), with several modifications. Kidneys from 15–20 animals were obtained, and the cortex was dissected away and frozen at −80° C. Frozen tissue (2000–2500 g) was homogenized in 12 L of 0.25 M sucrose in a Waring blender. The homogenate then was left at 37° C. for 18 hours to facilitate cleavage of DP-4 from cell membranes. After the cleavage step, the homogenate was clarified by centrifugation at 7000×g for 20 minutes at 4° C., and the supernatant was collected. Solid ammonium sulfate was added to 60% saturation, and the precipitate was collected by centrifugation at 10,000×g and was discarded. Additional ammonium sulfate was added to the supernatant to 80% saturation, and the 80% pellet was collected and dissolved in 20 mM $Na_2HPO4$, pH 7.4.

After dialysis against 20 mM $Na_2HPO4$, pH 7.4, the preparation was clarified by centrifugation at 10,000×g. The clarified preparation then was applied to 300 ml of ConA Sepharose that had been equilibrated in the same buffer. After washing with buffer to a constant $A_{280}$, the column was eluted with 5% (wt/vol) methyl α-D-mannopyranoside. Active fractions were pooled, concentrated, and dialyzed against 5 mM sodium acetate, pH 5.0. Dialyzed material then was flowed through a 100 ml Pharmacia Resource S column equilibrated in the same buffer. The flow through material was collected and contained most of the enzyme activity. Active material again was concentrated and dialyzed into 20 mM $Na_2HPO4$, pH 7.4. Lastly, the concentrated enzyme was chromatographed on a Pharmacia S-200 gel filtration column to removed low molecular weight contaminants. Purity of column fractions was analyzed by reducing SDS-PAGE, and the purest fractions were pooled and concentrated. Purified enzyme was stored in 20% glycerol at −80° C.

Assay of Porcine Dipeptidyl Peptidase IV

Enzyme was assayed under steady-state conditions as previously described (2) with gly-pro-p-nitroanilide as substrate, with the following modifications. Reactions contained, in a final volume of 100 μl, 100 mM Aces, 52 mM TRIS, 52 mM ethanolamine, 500 μM gly-pro-p-nitroanilide, 0.2% DMSO, and 4.5 nM enzyme at 25° C., pH 7.4. For single assays at 10 μM test compound, buffer, compound, and enzyme were added to wells of a 96 well microtiter plate, and were incubated at room temperature for 5 minutes. Reactions were started by addition of substrate. The continuous production of p-nitroaniline was measured at 405 nM for 15 minutes using a Molecular Devices Tmax plate reader, with a read every 9 seconds. The linear rate of p-nitroaniline production was obtained over the linear portion of each progress curve. A standard curve for p-nitroaniline absorbance was obtained at the beginning of each experiment, and enzyme catalyzed p-nitroaniline production was quantitated from the standard curve. Compounds giving greater than 50% inhibition were selected for further analysis.

For analysis of positive compounds, steady-state kinetic inhibition constants were determined as a function of both substrate and inhibitor concentration. Substrate saturation curves were obtained at gly-pro-p-nitroanilide concentrations from 60 μM to 3600 μM. Additional saturation curves also were obtained in the presence of inhibitor. Complete inhibition experiments contained 11 substrate and 7 inhibitor concentrations, with triplicate determinations across plates. For tight binding inhibitors with $K_i$s less than 20 nM, the enzyme concentration was reduced to 0.5 nM and reaction times were increased to 120 minutes. Pooled datasets from the three plates were fitted to the appropriate equation for either competitive, noncompetitive or uncompetitive inhibition.

(1) Rahfeld, J. Schutkowski, M., Faust, J., Neubert., Barth, A., and Heins, J. (1991) Biol. Chem. Hoppe-Seyler, 372, 313–318

(2) Nagatsu, T., Hino, M., Fuyamada, H., Hayakawa, T., Sakakibara, S., Nakagawa, Y., and Takemoto, T. (1976) Anal. Biochem., 74, 466–476

The following abbreviations are employed in the Examples and elsewhere herein:

Ph=phenyl
Bn=benzyl
i-Bu=iso-butyl
Me=methyl
Et ethyl
TMS=trimethylsilyl
FMOC=fluorenylmethoxycarbonyl
Boc=tert-butoxycarbonyl
Cbz=carbobenzyloxy or carbobenzoxy or benzyloxycarbonyl
HOAc or AcOH=acetic acid
TFA=trifluoroacetic acid
$Et_2NH$=diethylamine
NMM=N-methyl morpholine
n-BuLi=n-butyllithium
Pd/C=palladium on carbon
$PtO_2$=platinum oxide
TEA=triethylamine
EDAC=3-ethyl-3'-(dimethylamino)propyl-carbodiimide hydrochloride (or 1-[(3-(dimethyl)amino)propyl])-3-ethylcarbodiimide hydrochloride)
HOBT or $HOBT.H_2O$=1-hydroxybenzotriazole hydrate
HOAT=1-hydroxy-7-azabenzotriazole
PyBOP reagent=benzotriazol-1-yloxy-tripyrrolidino phosphonium hexafluorophosphate
min=minute(s)
h or hr=hour(s)
L=liter
mL=milliliter
FL=microliter
g=gram(s)
mg=milligram(s)
mol=moles
mmol=millimole(s)
meq=milliequivalent
RT=room temperature
sat or sat'd=saturated
aq.=aqueous TLC=thin layer chromatography
HPLC=high performance liquid chromatography
LC/MS=high performance liquid chromatography/mass spectrometry
MS or Mass Spec=mass spectrometry
NMR=nuclear magnetic resonance
mp–melting point The following Examples represent preferred embodiments of the invention.

EXAMPLE 1

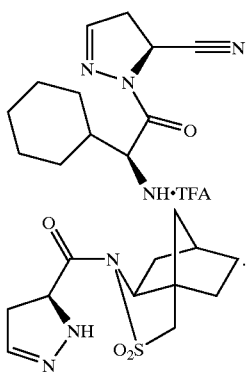
A

The Part A compound was prepared by following the literature procedure described by Mish, Michael R.; Guerra, Francisco M.; Carreira, Erick M.; J. Am. Chem. Soc. (1997), 119, 8379–8380.

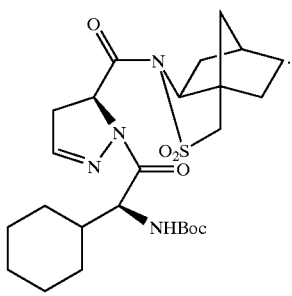
B

To a stirred solution of part A compound (54.4 mg, 0.175 mmol) in (CH$_2$Cl)$_2$ (1 mL) at room temperature under nitrogen was added (S)-N-t-butoxycarbonyl-cyclohexylglycine (90 mg, 0.35 mmol), HOAt (47 mg, 0.35 mmol), Et$_3$N (24 μL, 0.17 mmol) and EDAC (66.6 mg, 0.35 mmol). The resulting yellow solution was stirred at room temperature for 5 days. The solution was diluted with EtOAc and washed twice with saturated NaHCO$_3$ solution. The organic extracts were combined, dried (MgSO$_4$) and evaporated. Purification by flash chromatography (2.5×5 cm column, 1:19 EtOAc/CH$_2$Cl$_2$) gave the title compound as a colorless oil, 30.3 mg, 31% yield. LC/MS gave the correct molecular ion [(M+H)$^+$=523] for the desired compound.

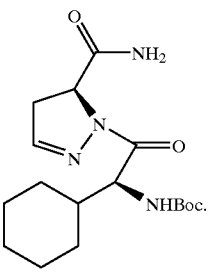
C

A solution of part B compound (403 mg, 0.73 mmol) in methanolic ammonia (2 M, 5 mL, 10 mmol) was stirred at room temperature in a sealed glass tube for 24 h. The reaction mixture was evaporated and the residue purified by flash chromatography (2.5×5 cm column, EtOAc) to give the title compound as a white solid, 150 mg, 58% yield. LC/MS gave the correct molecular ion [(M+H)$^+$=353] for the desired compound.

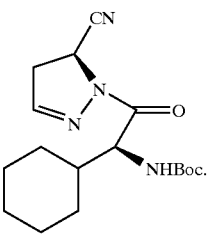
D

To a stirred solution of part C compound (44.0 mg, 0.125 mmol) and imidazole (17.1 mg, 0.25 mmol) in pyridine (2.5 mL) at −35° C. under nitrogen was added POCl$_3$ (52 μL, 0.56 mmol) at a rate to keep the temperature below −20° C. After 1 h at −20° C. the reaction mixture was warmed to room temperature and evaporated. The residue was partitioned between EtOAc and 5% KHSO$_4$ solution. The organic extract was dried (MgSO$_4$) and evaporated to give the title compound as a white solid, 40 mg, 96% yield. LC/MS gave the correct molecular ion [(M+H)$^+$=335] for the desired compound.

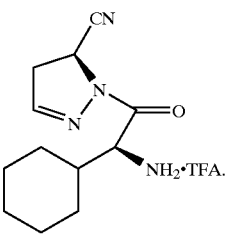
E

To a stirred solution of part D compound (40 mg, 0.12 mmol) in CH$_2$Cl$_2$ (1 mL) at room temperature was added trifluoroacetic acid (1 mL). The reaction mixture was stirred at room temperature for 30 min. The reaction mixture was added slowly to a precooled slurry of NaHCO$_3$ (0.8 g) in H$_2$O (3 mL). The mixture was extracted with CH$_2$Cl$_2$ (5 mL×3), and the combined CH$_2$Cl$_2$ extracts were evaporated and purified by reverse phase preparative HPLC (MeOH/H₂O/TFA) to give the title compound as a white amorphous solid, 32 mg. 77% yield. LC/MS gave the correct molecular ion [(M+H)⁺=235] for the desired compound.

EXAMPLE 2

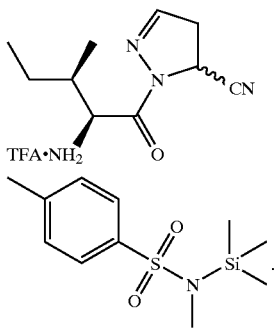

A

To a stirred solution of N-methyl-p-tolylsulfonamide (3.77 g, 20.4 mmol) in toluene (40 mL) and acetonitrile (40 mL) at room temperature under nitrogen was added chlorotrimethylsilane (12.3 mL, 96.9 mmol). The solution was cooled to 0° C. and a solution of triethylamine (3.30 mL, 23.7 mmol) in toluene (10 mL) was added at a rate to keep the temperature below 6° C. After addition was completed, the reaction was allowed to warm to room temperature and stirred for 14 h. The resulting slurry was filtered, washing with toluene. The filtrate was evaporated and the residue slurried in ether, filtered and re-evaporated to give the title compound as an orange oil, 5.15 g, 98%.

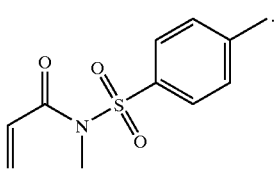

B

To a stirred solution of part A compound (5.15 g, 20.0 mmol) in toluene (25 mL) at room temperature under nitrogen was added acryloyl chloride (6.6 mL, 81 mmol) and cupric chloride (270 mg, 2 mmol). The reaction was heated to 80° C. for 16 h, then filtered hot and evaporated twice from toluene. The residue was dissolved in acetonitrile (30 mL) and treated with potassium carbonate (1.38 g, 10.0 mmol). After refluxing for 1 h, the reaction mixture was cooled, diluted with CH₂Cl₂ (100 mL), filtered and evaporated. Purification by flash chromatography (5×20 cm column, 27:73 EtOAc/hexanes) gave the title compound as a colorless oil, 4.47 g, 90% yield. LC/MS gave the correct molecular ion [(M+H)⁺=240] for the desired compound.

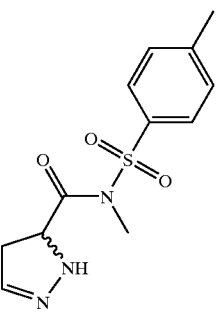

C

To a solution of part B compound (2.08 g, 8.70 mmol) in toluene (100 mL) stirred at room temperature under nitrogen was added a solution of trimethylsilyl-diazomethane (10 mL, 20 mmol, 2 M in hexanes). After 20 h, the reaction mixture was evaporated, dissolved in CH₂Cl₂ and at room temperature under nitrogen, treated with TFA (0.85 mL, 11 mmol) and stirred for 1 h. The solution was washed once with saturated sodium bicarbonate solution, dried (Na₂SO₄) and evaporated. Purification by flash chromatography (5×20 cm column, 1:4 hexanes/EtOAc) gave the title compound as a colorless oil, 1.77 g, 72% yield. LC/MS gave the correct molecular ion [(M+H)⁺=282] for the desired compound.

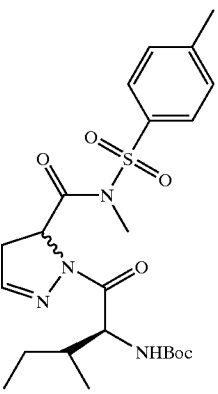

D

To a stirred solution of N-t-butoxycarbonyl-(S)-isoleucine (518 mg, 2.24 mmol), N-methylmorpholine (0.50 mL, 4.5 mmol) and PyBOP (1.75 g, 3.35 mmol) in CH₂Cl₂ (9 mL) under nitrogen at room temperature was added a solution of part C compound (630 mg, 2.24 mmol) in CH₂Cl₂ (3 mL). After 87 h, approximately half the starting materials had been consumed. The reaction was diluted CH₂Cl₂ and washed once with 5% potassium hydrogen sulfate solution. The organic extract was dried (MgSO₄) and evaporated. Purification by flash chromatography on silica gel (5×15 cm column, 3:7 EtOAc/hexanes) gave the title compound as a white amorphous solid, 287 mg, 26% yield. LC/MS gave the correct molecular ion [(M+H)⁺=495] for the desired compound.

E

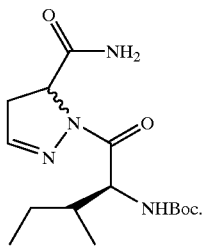

To a stirred solution of Part D compound (280 mg, 0.57 mmol) in THF (2 mL) at room temperature was added methanolic ammonia (2 M, 2 mL). The reaction mixture was heated to 80° C. in a sealed tube for 15 h. The reaction mixture was evaporated and re-evaporated from hexanes to give a gummy oil. Purification by flash chromatography on silica gel (5×10 cm column, EtOAc) gave the title compound as a 21:79 mixture of diastereomers, 116 mg, 63%. LC/MS gave the correct molecular ion [(M+H)$^+$=327] for the desired compound.

F

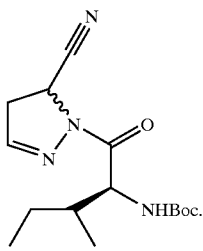

To a stirred solution of Part E compound (92.3 mg, 0.283 mmol) and imidazole (39 mg, 0.57 mmol) in pyridine (2.5 mL) at −35° C. under nitrogen was added POCl$_3$ (106 μL, 1.14 mmol) at a rate to keep the temperature below −20° C. After 1 h at −20° C. the reaction mixture was warmed to room temperature and evaporated. The residue was partitioned between EtOAc and 5% KHSO$_4$ solution. The organic extract was dried (MgSO$_4$) and evaporated. Purification by flash chromatography on silica gel (2.5×5 cm column, 1:1 EtOAc/hexanes) gave the title compound as a white solid, 28.5 mg, 32% yield. LC/MS gave the correct molecular ion [(M+H)$^+$309] for the desired compound.

G

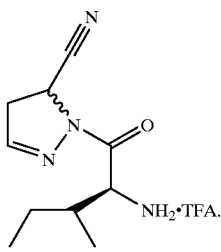

To a stirred solution of Part F compound (28.5 mg, 0.091 mmol) in CH$_2$Cl$_2$ (0.2 mL) at room temperature under nitrogen was added TFA (0.2 mL). After 40 min, the reaction was evaporated, dissolved in water (5 mL) and lyophilized. Purification by gradient reverse phase HPLC and lyophilization gave the title compound as a white hygroscopic solid, 14.5 mg, 49% yield. LC/MS gave the correct molecular ion [(M+H)$^+$=209] for the desired compound as its free base.

EXAMPLE 3

A

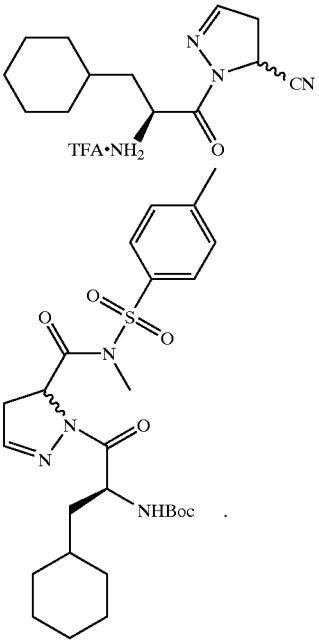

To a stirred solution of Example 2 Part C compound (1.047 g, 3.72 mmol), N-t-butoxycarbonyl-(S)-cyclohexylanaline (1.085 g, 4.00 mmol), N-methylmorpholine (0.2 mL, 0.2 mmol), HOAt (600 mg, 4.4 mmol) and DMAP (50 mg, 0.4 mmol) in THF (15 mL) under nitrogen at room temperature was added EDAC (843 mg, 4.4 mmol). After 96 h, the reaction was diluted with EtOAc and washed once with saturated sodium bicarbonate solution. The organic extract was dried (MgSO$_4$) and evaporated. Purification by flash chromatography on silica gel (5×12 cm column, 1:2 EtOAc/hexanes) gave the title compound as a white amorphous solid, 1.02 g, 51% yield. LC/MS gave the correct molecular ion [(M+H)$^+$=535] for the desired compound.

B

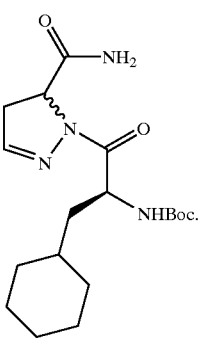

To a stirred solution of Part A compound (904 mg, 1.69 mmol) in THF (8 mL) at room temperature was added methanolic ammonia (2 M, 8 mL). The reaction mixture was heated to 80° C. in a sealed tube for 14 h. The reaction mixture was evaporated and re-evaporated from CH$_2$Cl$_2$ to give a gummy oil. Purification by flash chromatography on silica gel (5×15 cm column, 1:49 MeOH/EtOAc) gave the title compound as a 2:1 mixture of diastereomers, 526 mg, 85%. LC/MS gave the correct molecular ion [(M+H)$^+$=367] for the desired compound.

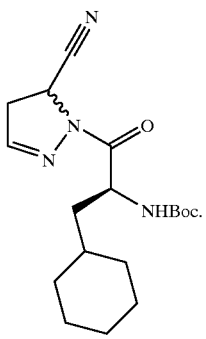

To a stirred solution of part B compound (525 mg, 1.43 mmol) and imidazole (194 mg, 2.86 mmol) in pyridine (25 mL) at −35° C. under nitrogen was added POCl$_3$ (0.58 mL, 5.7 mmol) at a rate to keep the temperature below −20° C. After 1 h at −20° C. the reaction mixture was warmed to room temperature and evaporated. The residue was partitioned between EtOAc and 5% KHSO$_4$ solution. The organic extract was dried (MgSO$_4$) and evaporated. Purification by flash chromatography on silica gel (5×15 cm column, 17:3 EtOAc/hexanes) gave the title compound as a white solid, 410 mg, 82% yield. LC/MS gave the correct molecular ion [(M+H)$^+$=349] for the desired compound.

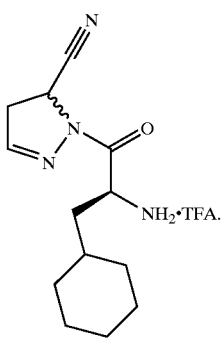

To a stirred solution of Part C compound (141 mg, 0.4 mmol) in CH$_2$Cl$_2$ (0.4 mL) at room temperature under nitrogen was added TFA (0.4 mL). After 4 h, the reaction was evaporated, dissolved in water (5 mL) and lyophilized. Purification by gradient reverse phase HPLC and lyophilization gave the title compound as a white hygroscopic solid, 94 mg, 65% yield. LC/MS gave the correct molecular ion [(M+H)$^+$=249] for the desired compound as its free base.

EXAMPLE 4

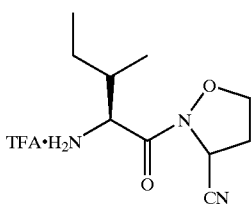

C

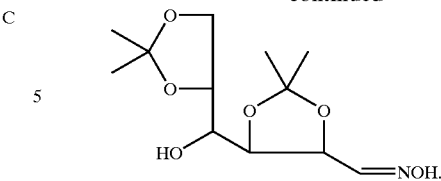

A solution of 2,3:5,6-Di-O-isopropylidene-α-D-mannofuranose (1.0 g, 3.84 mmol) in dry CH$_2$Cl$_2$ (15 ml) under nitrogen was treated with hydroxylamine hydrochloride (267 mg, 3.84 mmol) followed by triethylamine (0.515 ml, 3.84 mmol). After stirring at room temperature for 3 days, additional hydroxylamine hydrochloride (134 mg, 1.92 mmol) and Et$_3$N (0.20 ml, 1.5 mmol) was added and the reaction mixture stirred at room temperature for another 24 h. The reaction mixture was filtered, washed with water (10 ml) and 5% aqueous sodium bicarbonate (10 ml), then dried (MgSO$_4$) and evaporated to give the title compound as a white gum, 500 mg, 47% yield. Rf=0.56 and 0.48 for both isomers (Silica gel; EtOAc:Hexane−1:1, Anisaldehyde). LC/MS gave the correct molecular ion [(M+H)$^+$=276] for the desired compound.

B

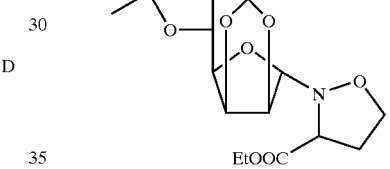

According to literature procedure (JCS Chem. Commun. 1981, 97), a mixture of Part A compound (D-Mannose oxime; 2.61 g, 9.55 mmol) and ethyl glyoxal (50% solution in toluene; 6.0 ml or 3.06 g, 3.0 eq) in chloroform (10 ml) were subjected to ethylene gas in a bomb, keeping the temperature at 75° C. and the pressure at 58 bar for 17 h. (Leakage caused a drop in pressure after 3.0 h). The bomb was cooled, vented and the reaction mixture concentrated. Flash chromatography on silica gel (1:9 EtOAc/hexanes, then 1:4 EtOAc/hexanes) gave the title compound as a clear syrup, 2.91 g, 78%. R$_f$=0.58 (Silica gel; EtOAc:Hexane-1:1, Anisaldehyde). LC/MS gave the correct molecular ion [(M+H)$^+$=389] for the desired compound.

C

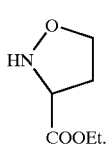

A solution of Part B compound (1.33 g, 3.42 mmol) in 6% aqueous methanol (30 ml) was treated with 1.0 N hydrochloric acid (3.86 ml, 3.86 mmol) and heated to 40° C. for 4 h. The mixture was cooled and concentrated and the residual oil diluted with water (9 ml). The aqueous solution was neutralized with aqueous sodium carbonate (2.0 M, 1.25 ml, 2.5 mmol), extracted with EtOAc (3×25 ml) and the combined extracts were washed with brine (5 ml), dried (MgSO$_4$) and concentrated. Flash chromatography on silica gel (1:19 MeOH/CH$_2$Cl$_2$) gave the title compound as a clear syrup, 518 mg, 100%. R$_f$=0.62 (Silica gel; CH$_2$Cl$_2$:CH$_3$OH-9:1). LC/MS gave the correct molecular ion [(M+H)$^+$=146] for the desired compound.

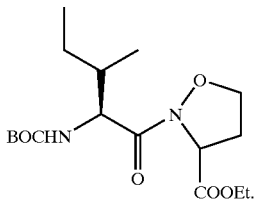

D

A solution of BOC-L-isoleucine (791.4 mg, 3.42 mmol) in dry CH$_2$Cl$_2$ (10 ml) was cooled to 0° C. and treated under nitrogen with 4-methylmorpholine (0.38 ml, 3.42 mmol), HOBt.H$_2$O (463.4 mg, 3.42 mmol) and 1-(3-dimethylaminopropyl)-3-ethylcarbodiimide hydrochloride (658.8 mg, 3.42 mmol). The reaction mixture was stirred at 0° C. for 1 h then treated with a solution of Part C compound (518.2 mg, 3.42 mmol) in dry CH$_2$Cl$_2$ (10 ml). The reaction mixture was stirred at 0° C. for 1 h then at room temperature for 19 h. 4-Dimethylaminopyridine (417.8 mg, 3.42 mmol) was added and stirring continued at room temperature for another 24 h. The reaction mixture was concentrated and the residual syrup partitioned between EtOAc (3×50 ml) and water (15 ml). The combined organic extracts were washed with brine (10 ml), dried (MgSO$_4$), filtered and concentrated. Flash chromatography on silica gel (1:4 EtOAc/hexanes, then 1:2 EtOAc/hexanes) gave a mixture (1:1) of isomers. Further purification of each isomer by preparative HPLC gave the title compound as a mixture of two diastereomers, 249 mg, 20%, a clear syrup. LC/MS gave the correct molecular ions [(M+Na)=381] for Isomer A and [(M+H)$^+$=359] for Isomer B.

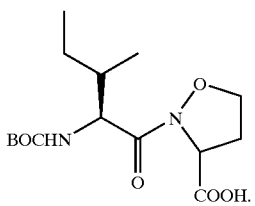

E

A solution of Part D compound (249.4 mg, 0.70 mmol) in 1:1 MeOH/H$_2$O (6.2 ml) was treated with lithium hydroxide monohydrate (45.2 mg, 1.05 mmol) and stirred at room temperature under nitrogen for 24 h and evaporated. The syrup obtained was re-dissolved in water (17 ml), extracted with ether (20 ml), acidified to pH 3.0 with 10% aqueous citric acid (4.4 ml) and extracted with EtOAc (3×40 ml). The EtOAc extracts were combined, washed with brine (12 ml), dried (Na$_2$SO$_4$), and concentrated to give the diastereomeric title compound as a clear syrup, 249.8 mg, 100%. R$_f$=0.08 (Silica gel; EtOAc:Hexane, 1:1, Ninhydrin). LC/MS gave the correct molecular ion [(M+Na)=353] for both isomers of the desired compound.

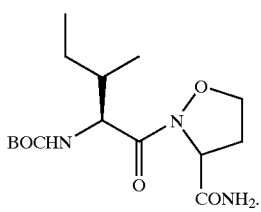

F

A solution of Part E compound (228 mg, 0.69 mmol) in dry THF(6 ml) was cooled to −15° C. under nitrogen, treated with 4-methylmorpholine (0.091 ml, 0.83 mmol) and isobutylchloroformate (0.099 ml, 0.76 mmol) then stirred at −15° C. for 30 min. A solution of ammonia in dioxane (0.5 M, 6.9 ml, 5.0 eq) was added and stirring continued at −15° C. for 30 min and then at room temperature for 20 h. The reaction mixture was partitioned between EtOAc (3×25 ml) and 5% potassium bisulfate solution (5 ml) and the organic phase was washed with brine (5 ml), dried over anhydrous sodium sulfate, filtered and concentrated. Preparative HPLC gave the title compound as a solid foam, 124.7 mg, 55%. R$_f$=0.25 and 0.18 for both isomers (Silica gel; EtOAc:Hexane−4:1, Ninhydrin). LC/MS gave the correct molecular ion [(M+Na)=352] for both isomers of the desired compound.

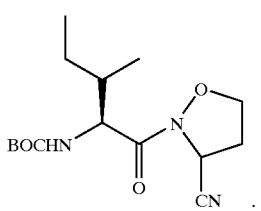

G

A mixture of Part F compound (124.7 mg, 0.387 mmol) and imidazole (53.1 mg, 0.78 mmol) in dry pyridine (5.5 ml) was cooled to −30° C. under nitrogen, treated with phosphorous oxychloride (0.14 ml, 1.5 mmol) and stirred at −20° C. to −30° C. for 1 h under nitrogen. The mixture was stripped to dryness and the residual solid sequentially evaporated from methylene chloride (13 ml) and ether (19 ml). Flash chromatography with 25% ethyl acetate in hexane (1.2 L) gave the title compound as a mixture of diastereomers in the form of a syrup, 72.2 mg, syrup, 60%. R$_f$=0.62 and 0.55 for both isomers (Silica gel; EtOAc:Hexane−1:1, Ninhydrin). LC/MS gave the correct molecular ion [(M+Na)=334] for both isomers of the desired compound.

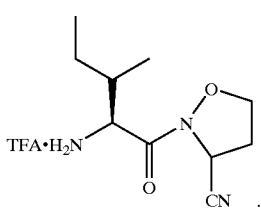

H

A solution of Part G compound (72.2 mg, 0.23 mmol) in dry dichloromethane (0.81 ml) and trifluoroacetic acid (0.81 ml) was stirred at room temperature under nitrogen for 2 h. The reaction mixture was concentrated and the resulting syrup evaporated sequentially from toluene (10 ml) and ether (2×10.0 ml). The crude product was purified by preparative reverse phase HPLC to give the title compound as a mixture of isomers in the form of a syrup, 14.2 mg, 19%. $R_f$=0.38 (Silica gel; $CH_2Cl_2$:$CH_3OH$-9:1, Ninhydrin). LC/MS gave the correct molecular ion [(M+H)$^+$=212] for the desired compound.

EXAMPLE 5 to 13

Following the procedures of Examples 1 to 4 and the reaction schemes set out above, the following compounds may be prepared.

| Ex. No. | R³ | n | R⁴ | R² | R¹ | | Y═══Z | X |
|---------|-----|---|-----|------|------|---|-------|-----|
| 5 | H | 0 | — | | H | (3-hydroxyadamantyl) | N═CH | CN |
| 6 | H | 0 | — | | H | (cyclopentyl) | N—CH₂ | H |
| 7 | C₂H₅ | 1 | H | C₂H₅ | | (bicyclic) | O—CH₂ | CN |
| 8 | H | 1 | H | | H | (cyclopropyl) | N═CH | H |
| 9 | CH₃ | 1 | CH₃ | CH₃ | | (cyclopentyl) | NH—CH₂ | CN |
| 10 | H | 0 | — | | H | (bicyclo[2.2.2]) | NH—CH₂ | H |
| 11 | H | 0 | — | | H | (1-hydroxymethyl cyclopentyl) | N═CH | CN |
| 12 | H | 1 | H | CH₃ | H | | O—CH₂ | H |
| 13 | CH₃ | 1 | CH₃ | C₂H₅ | CH₃ | | NH—CH₂ | CN |

What is claimed is:
1. A compound having the structure

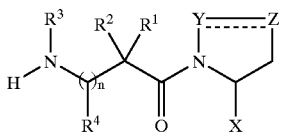

n is 0;
X is CN;
Y is N or NH;
Z is CH or $CH_2$, with Z being $CH_2$ when Y is NH, with Y—Z forming a single bond, and Z being CH when Y is N, with Y—Z forming a double bond;

$R^1$, $R^2$, $R^3$ and $R^4$ are the same or different and are independently selected from hydrogen, alkyl, alkenyl, alkynyl, cycloalkyl, cycloalkylalkyl, bicycloalkyl, bicycloalkylalkyl, alkylthioalkyl, arylalkylthioalkyl, cycloalkenyl, aryl, aralkyl; all optionally substituted through available carbon atoms with 1, 2, 3, 4 or 5 groups selected from hydrogen, halo, alkyl, polyhaloalkyl, alkoxy, haloalkoxy, polyhaloalkoxy, alkoxycarbonyl, alkenyl, alkynyl, cycloalkyl, cycloalkylalkyl, polycycloalkyl, arylamino, hydroxy, hydroxyalkyl, nitro, cyano, amino, substituted amino, alkylamino, dialkylamino, thiol, alkylthio, alkylcarbonyl, acyl, alkoxycarbonyl, aminocarbonyl, alkynylaminocarbonyl, alkylaminocarbonyl, alkenylaminocarbonyl, alkylcarbonyloxy, alkylcarbonylamino, arylcarbonylamino, alkylsulfonylamino, alkylaminocarbonylamino, alkoxycarbonylamino, alkylsulfonyl, aminosulfinyl, aminosulfonyl, alkylsulfinyl, sulfonamido or sulfonyl;

and $R^1$ and $R^3$ may optionally be taken together to form —$(CR^5R^6)_m$— where m is 2 to 6, and $R^5$ and $R^6$ are the same or different and are independently selected from hydroxy, alkoxy, H, alkyl, alkenyl, alkynyl, cycloalkyl, cycloalkylalkyl, cycloalkenyl, aryl, arylalkyl, alkylcarbonylamino, arylcarbonylamino, alkoxycarbonylamino, aryloxycarbonylamino, alkoxycarbonyl, aryloxycarbonyl, or alkylaminocarbonylamino, or $R^1$ and $R^4$ may optionally be taken together to form —$(CR^7R^8)_p$— wherein p is 3 to 6, and $R^7$ and $R^8$ are the same or different and are independently selected from hydroxy, alkoxy, cyano, H, alkyl, alkenyl, alkynyl, cycloalkyl, cycloalkylalkyl, cycloalkenyl, aryl, arylalkyl, alkylcarbonylamino, arylcarbonylamino, alkoxycarbonylamino, aryloxycarbonylamino, alkoxycarbonyl, aryloxycarbonyl, or alkylaminocarbonylamino, all stereoisomers thereof;
and a pharmaceutically acceptable salt thereof.

2. The compound as defined in claim 1 having the structure

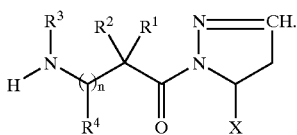

3. The compound as defined in claim 1 having the structure

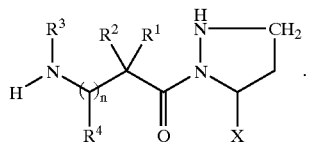

4. The compound as defined in claim 1 having the structure

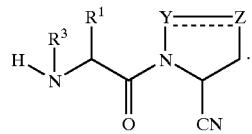

5. The compound as defined in claim 1 having the structure

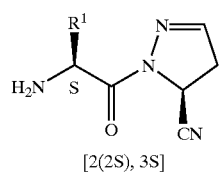

[2(2S), 3S]

wherein $R^1$ is H, alkyl, cycloalkyl or bicycloalkyl.

6. The compound as defined in claim 1 wherein $R^3$ is H or alkyl, $R^1$ is H, alkyl, cycloalkyl or bicycloalkyl, $R^2$ is H or alkyl, n is 0, and X is CN.

7. The compound as defined in claim 1 wherein X is CN and has the configuration

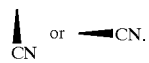

8. The compound as defined in claim 1 having the structure

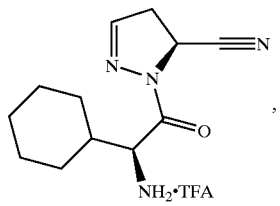

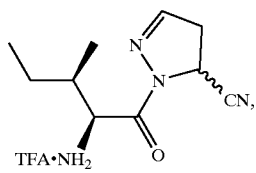

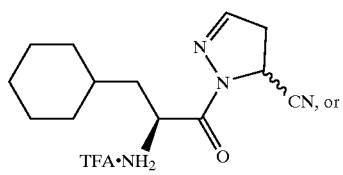

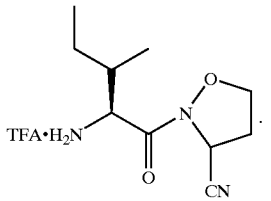

9. A pharmaceutical composition comprising a compound as defined in claim 1 and a pharmaceutically acceptable carrier therefor.

* * * * *